United States Patent [19]

Iaccheri et al.

[11] Patent Number: 4,842,995
[45] Date of Patent: Jun. 27, 1989

[54] DIAGNOSTIC METHOD FOR THE EVALUATION OF CLINICAL PARAMETERS BY DIRECT COLLECTION OF BIOLOGICAL MATERIALS AND DEVICE FOR ITS ACCOMPLISHMENT

[75] Inventors: Ennio Iaccheri; Paola Piro, both of Milan, Italy

[73] Assignee: Boehringer Biochemia Robin, S.p.A., Milan, Italy

[21] Appl. No.: 921,053

[22] PCT Filed: Dec. 5, 1985

[86] PCT No.: PCT/EP85/00675
§ 371 Date: Jul. 31, 1986
§ 102(e) Date: Jul. 31, 1986

[87] PCT Pub. No.: WO86/03590
PCT Pub. Date: Jun. 19, 1986

[30] Foreign Application Priority Data

Dec. 6, 1984 [IT] Italy ................................ 23926 A/84

[51] Int. Cl.$^4$ .................. C12Q 1/70; A61B 5/00; B65D 71/00
[52] U.S. Cl. .................................. 435/5; 128/769; 128/770; 422/57; 422/61; 435/7; 435/805; 435/810; 436/531; 436/808; 436/810

[58] Field of Search ............. 435/7, 5, 805, 810; 436/531, 808, 810; 422/61, 57; 128/769, 770

[56] References Cited

U.S. PATENT DOCUMENTS

| | | | |
|---|---|---|---|
| 3,926,521 | 12/1975 | Ginzel | 356/246 |
| 3,992,631 | 11/1976 | Harte | 436/800 |
| 4,657,869 | 4/1987 | Richards et al. | 435/287 |
| 4,720,455 | 1/1988 | Babu et al. | 435/7 |

Primary Examiner—Christine M. Nucker
Attorney, Agent, or Firm—Armstrong, Nikaido, Marmelstein, Kubovcik & Murray

[57] ABSTRACT

This invention relates to a device for the diagnostic evaluation of clinical parameters by direct collection of biological materials consisting of a solid support, of suited materials, shape and size, carrying fixed on its surface a pre-established quantity of an antibody, in the case that the substance to be assessed is an antigen, and of an antigen in the case that the substance to be determined is an antibody, as well as the related diagnostic method.

The biological material, collected as above specified, is subsequently qualitatively or quantitatively analyzed by conventional techniques.

2 Claims, 1 Drawing Sheet

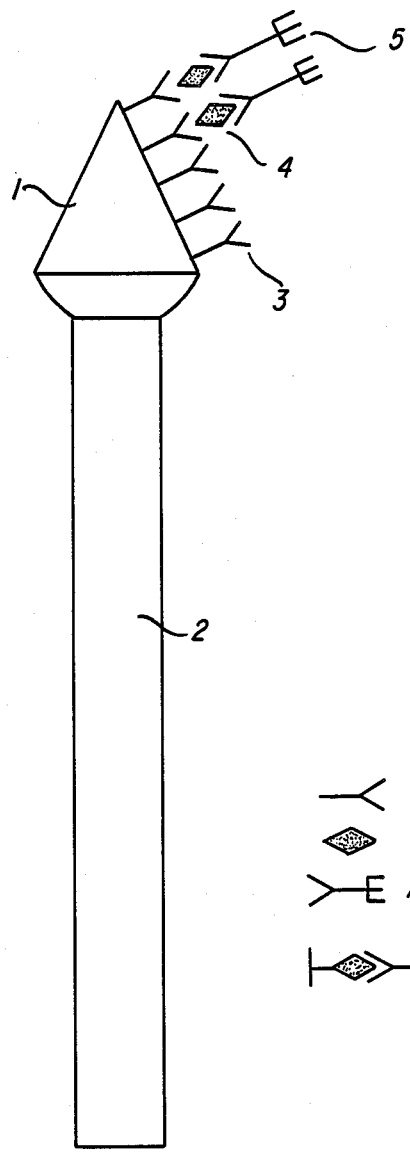

DIAGNOSTIC METHOD FOR THE EVALUATION OF CLINICAL PARAMETERS BY DIRECT COLLECTION OF BIOLOGICAL MATERIALS AND DEVICE FOR ITS ACCOMPLISHMENT

This invention relates to a diagnostic method, and to a related device for the assessment of clinical parameters, by direct collection of biological materials.

The device of the invention consists of a solid support (of a suited nature, shape and size), carrying fixed on its surface, by a suited technique, a pre-established quantity of an antigen or of an antibody or, in any case, of a substance able to inter-react with the compound to be determined in said biological materials. The diagnostic method of the invention consists in contacting said device with the biological tissues containing the antibodies or the antigens to be analyzed. The agglutinated product formed and fixed on the device is then enzymatically labelled by reaction with a specific antibody or antigen conjugated with an enzyme; after removal of the labelled antigens or antibodies not specifically bound by means of washings (for instance with water), the device is dipped in a suitable detecting solution containing a substrate for the labelling enzyme which is able to give a reaction useful for qualitative and/or quantitative measurements.

Literature data state that the assessment of many parameters of a clinical interest, by analysis of a biological fluid, requires the transfer of an exactly measured quantity into a suited container where it shall be incubated with a pre-established quantity of reagents so as to produce a detecting reaction.

While the conventional methods involve no specific difficulties when the biological materials can be easily collected, and are available in a relatively high quantity, as it usually occurs in the case of urine and blood, a different situation occurs when analytical determinations have to be carried out on biological materials available in a small or very small quantity (exudates, pus, mucus, saliva, etc.) or of hard collection from histologically altered tissues and/or tissues in hardly accessible areas, e.g. pustules, syphilomas, ulcerations, etc.

The disadvantages of said previously mentioned technique are overcome by the device and by the method that are the object of the present invention, actually enabling the direct collection of the biological material to be examined with no resort to the measurement of the specimen. The specimen, actually, can be collected directly on the patient, or subsequently on the specimen of fluid or biological tissues collected according to one of the usual laboratory techniques.

Further objects of the invention are provided by a method and a device particularly suited for the diagnosis of viruses and for the analytical determination of progesterone in milk samples.

Presently, the only diagnostic methods available for the detection of viruses in biological tissues (for instance during viral infections or to evaluate possible healthy bearers in a population) are based on cell culture procedures, which require expensive apparatuses, trained personell, and a long time (3 or more days) for the evaluation of the results.

Said reasons make difficult timely diagnostic analysis which could be useful for the prevention of disease spreading, for epidemiological studies and, generally, for an early diagnosis of viral diseases.

Examples of viruses whose presence must be often detected, comprise herpes viruses (type 1 and 2), Hepstein-Barr virus, Varicella Zoster virus, hyman T-lymphocytes virus 3 (HTLV-3).

It is therefore highly desirable a method for the detection of said viruses which could be carried out, even in not specialized centers, by not highly trained or specialized personell and without particular apparatuses such as sterile rooms and so on.

The method according to the invention allows to overcome the disadvantages of the known methods: it is in fact particularly simple, unexpensive fast, safe and accurate.

Every virus can be detected according to the method of the present invention provided that a specific antibody and specific antibodies labelled with enzymes are available. The antibody against the virus to be determined is bound on the device of the present invention. After the agglutination reaction, the device is contacted with the antibody labelled with the enzyme and then immersed into the corresponding detecting solution after removal of the enzyme-labelled antibody not specifically bound.

In the case of herpes virus, for instance, a monoclonal or polyclonal anti-HVS is absorbed on a device having a shape suited for the direct sampling from the tissues (for instance a cutaneous blister).

250 Patients have been subjected to said diagnostic method, in comparison with the known cell culture procedures. The method of the invention proved to be extremely reliable and in complete agreement with the previous methods. The results were however obtained in only one hour while the cell culture methods required at least three days.

Analogously, a device suited for the detection of HTLV-3, a virus responsible of the disease known as aquired immuno deficiency syndrome (AIDS), can be prepared both for the analysis of blood samples of individual subjects and of blood from unknown donors.

Another important advantage of the present invention is that it is possible to detect the virus even in an inactive, not replicative phase while the cell culture methods require that the viruses can replicate, otherwise an activation (with consequent further operative difficulties) is needed.

A further preferred application and object of the invention is a method for the detection of progesterone in milk samples. In cow milk, high level of progesterone are present during the luteal phase; after luteolysis the progesterone level in the milk decreases and remain to low levels until the starting of ovulation.

Presently, these determinations are extensively used by farmers before artificial insemination, in connection with or in alternative to treatment with prostaglandine $F_{20}$ analogues for syncronization of farmers' animals. In many countries, the progesterone determined in milk samples, is based on RIA methods with radioactive labelled progesterone. Also in this case the determination of progesterone according to the invention can be carried out even by the same farmer and not-trained personell, without any radioactive risk and the use of particular equipments.

According to the invention, the device is contacted with the biological material to be examined, said device consisting essentially of a handgrip and an extremity, intended for coming into contact with the biological material, carrying fixed, by suited techniques, pre-established quantities of antibodies (or antigens), specific or partially specific for the antigene (antibody) compounds to be determined.

The antigens or the antibodies, fixed on the extremity of the device according to this invention, will consequently bind, by immunochemical reaction, with the antibodies or with the antigens present in the investigational material, in a rate proportional to the quantity contained in the material itself.

According to a preferred embodiment of the present invention, after washing with a suited solvent or solution in order to remove the substances not fixed by a specific bond to the antigen or to the antibody previously fixed to the device, a direct quantitative and/or qualitative determination of the investigational clinical parameter, shall be preferably accomplished resorting to already known techniques based for example on chemical, immunochemical, immunoenzymatic, enzymatic, etc., reactions.

The shape and the size of the device of this invention, and particularly those of the extremity coated with antibodies or antigens, are not by themselves critical for the nature of this invention, being obviously conditioned by the intended application and by the type of collection required for the analytical determination.

For example, should the collection be made by skin puncture, a device shall be conveniently used, characterized by a more or less pointed, but substantially conic, shape with an extremity coated with antibodies or antigens. On the other hand, should the collection require a simple contact with a tissue or a dipping into a biological fluid, the surface coated with the antibodies or with the antigens may present a cylindrical, spherical, ovoidal, conical or frusto-conical, etc., shape.

Should collection be made by skin puncture, finally, a device proves particularly suited, consisting of a metal core, coated if the case with plastic material, fitted at its extremity with a body coated with antibodies and/or antigens, of suited size and shape (for example, a 2-5 mm diameter spherule) from which a metal tip, suited for injection, juts out a few millimeters (for example 0.5-2 mm): in the course of its use, the metal tip will cause the biological fluid to leak out (for example, a drop of blood), and impregnate the body coated with the antibody and/or the antigen, being with it in an immediate contact because of the minimal distance.

As suited materials for the support to be coated, plastic materials can be used, able to bind antibodies or antigens by adsorption, according to the present invention, such as polyethylene, polypropylene, polystyrene, polyurethans, polyvinyl chloride, BUNA-N, nylon, polyacrylates, polymethacrylates, polytetrafluoroethylene resins (TEFLON®), phenol resins, polyacrylamides, DELRIN®, LEXAN®, cellulose derivatives, silicone derivatives, etc.

Said materials may also coat a metal core.

The bond of the antibody or of the antigen with the device of this invention may also be chemical should the constructive plastic material contain amino-, hydroxy-, carboxy-, or isocyano- functional groups suited to fix protein compounds by a chemical bond. The suited plastic material may be activated, if the case, by dipping it into a pH 9 buffered solution of glutaraldehyde, according to an already well-known technique, or according to other similar methods commonly known, for example, in the field of enzymes immobilization.

Metal materials may also be used, when previously subjected to such a process as to make them porous or able in any case to adsorb antibodies and/or antigens, for example by galvanic techniques for the deposit of colloidal gold or other metals in a colloidal form.

Examples of coating with an antibody or an antigen of said materials, by said methods, are described in the U.S. Pat. No. 4,003,988, and in the following papers:
(a) IMMUNOASSAY USING ANTIGEN-ENZYME CONJUGATES
B. K. Van Weemen and A. H. W. Schuurs
Febs Letters—Vol. 15, Number 3—June 1971—p. 232-5
(b) SOLID PHASE ANTIBODY ASSAY BY MEANS OF ENZYME CONJUGATED TO ANTI-IMMUNOGLOBULIN
P. Leinikki and Suvi Passila
J. Clin. Path., 1976, 29—p. 1116-20
(c) ENZYME-LINKED IMMUNOSORBENT ASSAY WITH POLYVALENT GONOCOCAL ANTIGEN
B. R. Brodeur, F. E. Ashton and B. B. Diena
The Journal of Medical Microbiology—Vol. 15, No. 1-1981—p. 1-9
(d) A MICROPLATE ENZYME-IMMUNOASSAY FOR TOXOPLASMA ANTIBODY
J. Clin. Path., 1976, 29, p. 150-3
(e) ENZYMOLOGY (Immobilized Enzymes, Antigens, Antibodies and Peptides—Preparation and Characterization—Vol. I—Ed. Howard H. Weetall—Marcel Dekker, Inc., New York (1975).

The antibody, or the antibodies, used according to the invention to coat the support, may be polyclonal or monoclonal, or, if the case, mixture thereof, and may be specific for one or more active sites of the antigen to be determined; moreover, this specificity may be directed on one or more antigens.

Both antibodies and antigens may be fixed on the support with no limits of quantity: however, a quantity suited for the intended type of analysis shall be chosen, ranging possibly between one picogram and one milligram per square centimeter.

Examples of possible applications of the device and of the method according to this invention, include the direct determination of viruses and/or bacteria, the determination of antibodies and/or antigens associated with a specific pathologic condition, the determination of the antibody titer following immunologic treatments, the determination of drugs and their metabolites, the determination of hormones, and the determination of common clinical parameters. The support may also be coated so as to enable the determination or the assay of various not necessarily related clinical parameters, e.g. the determination of chorionic gonadotropin and cocaine in the urine.

Usually, the detecting reaction is properly carried out by means of an antibody labelled with a suited enzyme, specific for the antigen-antibody complex fixed on the support after the specimen collection. For the purpose, the device, carrying the antigen-antibody complex fixed thereon, is washed with suited buffer and/or water solutions in order to remove the unspecifically bound antigen or antibody, and it subsequently dipped and incubated, for a suited time, in a solution of said antibody conjugated with an enzyme.

Said antibody solutions preferably contain nonionic, ionic, and amphoteric buffering and emulsionating agents with a concentration of enzyme-labelled antibody ranging from 0.01 to 0.005% weight. The enzyme-labelled antibody-antigen-antibody complex will consequently be fixed on the support: after removing a possible unspecifically bound labelled antibody, by washing with suited buffer and/or water solutions, dipping the support, treated as above specified, into a solution containing a suited chromogenic system based on a substrate for the enzyme, will enable a simple and direct antigenic determination of the product of the enzymatic reaction, through colorimetric, spectrophotometric or other various techniques.

The attached FIGURE, provided only for illustration purposes and not limiting therefore the invention, represents schematically the device of the invention.

The reference number 1 indicates the cone-shaped support coated with the antibody or with the antigen, intended to come into contact with the biological material; the stem 2 acts as a handgrip, and may be of such a shape and size as to make use quite easy and comfortable; 3, 4 and 5 indicate the antibody, the antigen and the enzyme-labelled antibody respectively.

The device of the invention, enabling also to avoid a precise determination of the quantity of biological material to be examined, also offers the advantage, within the sensitivity limits of the method, of a higher reliability and precision thanks also to the minimization of the experimental errors: the analysis, moreover, become more rapid and timely with no need of an expensive equipment, so that even a direct home-use of analytical kits can be foreseen.

For the purpose the devices, that are the object of this invention, shall be prepared under strict sterile conditions in suited aseptic premises, and finally introduced into suited sterile containers, e.g. glass test-butes sealed by sterilized stoppers.

The following not restrictive examples illustrate some possible applications of the method and of the device of the invention.

EXAMPLE 1

(a) Preparation of the device suited for the determination of the Herpès Virus (HSV)

Polyvinyl chloride pointers, with a cone-shaped extremity, were used as solid phase.

The extremity of said pointers was allowed to incubate with an anti-HSV-2 antiserum, diluted in a 1:300 ratio with 50 mM pH 9.6 carbonate/bicarbonate buffer. In terms of technical procedure, the antiserum was fixed to the support dipping the pointers' conical extremity into the wells of a polyvinyl chloride microdish containing 0.15 ml of antiserum so that the whole conical area could be dipped into the solution. The microdish was thereafter allowed to incubate for 2 hours at 37° C. in a wet chamber, and subsequently overnight at 4° C.

At the end of the incubation, the pointers were accurately washed with pH 7.4 saline phosphate buffer ($KH_2PO_4$ 15 mM, $Na_2HPO_4$ 85 mM, NaCl 15 mM, KCl 25 mM), containing Tween 0.05%, introduced into the wells of another dish containing the same saline buffer with 0.3% bovine serum albumin, and allowed to incubate for 1 hour at 37° C. in a wet chamber. This treatment has the purpose to saturate all possible polyvinyl chloride free sites that, in the following steps, may also be caused to adsorb the viral particles or the conjugated antiserum.

In a similar way a device for the determination of Hepstein-Barr virus, Varicella Zoster virus and Human T-Lymphocyte Virus-3 (HTLV) is prepared.

(b) "In Vitro" determination of HSV

After an identical step, the pointers were allowed to contact, for a short time at room temperature, a HSV virus suspension diluted 1:5 in saline (0.9% NaCl).

After washing, the pointers were introduced into glass test-tubes containing anti HSV-2 antiserum conjugated with peroxidase at a 1:150 dilution in saline phosphate buffer containing 0.05% of Tween 20. This procedure was followed by a 30–40 minutes incubation at room temperature, and by washing in saline phosphate buffer, containing 0.05% of Tween 20, in order to prevent possible analytical interferences of the conjugated antiserum unspecifically bound with the antigen.

After the last stage of treatment, the pointers were introduced into a chromogen solution consisting of 3.4 mg of ortho-phenylenediamine dissolved in 10 ml of buffer, formed by equal parts of 0.1M citric acid and 0.2M $Na_2HPO_4$, added, just before using, with 50 mcl of a 3% $H_2O_2$ solution.

The results recorded could state the good specificity and sensitivity of this technique: actually, the positive specimens show, through the chromogenic system, an intense color markedly distinguishable from the almost non-existent one of the negative specimens.

(c) Explanatory procedure of a HSV determination by direct collection

Herpes infections, Type 1, Type 2 or Types 1 and 2 occur usually with the formation of various-sized vesicles in the genital and/or labial area; the formation of herpetic vesicles in other bodily organs is more rare.

To the purpose of diagnosing an actual viral infection of a herpetic origin, the device, prepared according to the procedure as per item (a), is allowed to contact the vesicle with its lanceolated extremity, causing consequently the vesicle to break.

The device is subsequently rotated, and the fluid from the broken vesicle allowed to contact the anti HSV antibodies previously fixed on the pointer.

As soon as the fluid collection is terminated, the device is introduced into an ampul containing 300 mcl of a solution of anti HSV conjugated with peroxidase enzyme, and diluted in a 30 mM phosphate buffer containing 0.05 percent of Tween 20, and 1 per cent of bovine serum albumin.

After a 15-minute incubation, the support is washed with running water for about 60", and transferred into an ampul containing 300 mcl of a pH 5 solution characterized by the following percent composition (w/v):

Tetramethylbenzidine—0.02
Citric acid—2.10
Sodium Perborate—0.07
Sodium phosphate, dibasic—3.00
Dimethylsulfoxide—20.00
Distilled water—75.00

After a 15-minute incubation, the solution, contained in the ampul, is observed. It may be:

(a) colorless in the case of a negative result (absence of HSV in the patient's vesicle);
(b) blue in the case of a positive result (presence of HSV in the patient's vesicle).

EXAMPLE 2

Determination of the antistreptolysin O (ASO) Titer

The extremity of the support, previously coated with streptolysin, according to the technique used in the Example 1, is allowed to stand for some seconds in contact with the investigational serum or with a drop of whole blood collected from the forefinger's tip pierced by a normal self-injection apparatus, e.g. Autoclik. The extremity of the support is washed with water, and dipped into a solution containing an anti-IgG antibody labelled with an enzyme (serum alkaline phosphatase or peroxidase). The labelled anti IgG - streptolysin - antistreptolysin complex is consequently present on the surface and, dipped into a solution of the substrate (para-nitrophenylphosphate and azino-benzothiazolin-sulfonate), will color it more or less intensively depending on the antibody titer of the serum or of the blood.

EXAMPLE 3

Determination of morphine in the urine or in the blood

The previously indicated solid support, coated with an antimorphine antibody according to the technique specified in the Example 1, is dipped into the investigational urine or into a small investigational serum or blood specimen; after an incubation of about 15 minutes, the support is dipped into a solution of peroxidase-conjugated morphine in 30 mM phosphate buffer at pH 7. After a 10-minute incubation time, the support is thoroughly washed, and dipped into a test solution of tetramethylbenzidine and perborate prepared according to the Example 1 (c).

The intensity of the developed color is inversely proportional to the concentration of morphine present in the investigational biological fluid.

EXAMPLE 4

Determination of cocaine and human chorionic gonadotropin in the urine

The polyvinyl chloride or polystyrene support, of a spherical or ogival shape, is dipped for coating into a mixture of anti-benzoylecgonine (the major metabolite of cocaine in man) serum and human chorionic antigonadotropin serum.

The antisera used may be polyclonal (from rabbit and goat) or monoclonal (produced both in vitro and in vivo) or pools of both; the ratio of the two antisera in the mixture is properly selected according to the sensitivity to be attained in the determination of the two parameters.

The related dilutions, carried out in carbonate-dicarbonate buffer, may range between 1:50 and 1:50,000.

The coating time ranges between 30 minutes and 72 hours at a temperature ranging between $+4°-+60°$ C.

The support, as soon as coated with the antisera mixture, is saturated by applying a second coating with a solution of aspecificic immunoglobulins or in normal rabbit serum (in other cases also a bovine fetal serum may be used), in phosphate buffer, at a concentration ranging between 0.1 and 5 percent, under conditions of time and temperature as same as the ones used to coat the antisera mixture.

The support is subsequently washed in order to remove a possible excess of antibodies or proteins not fixed with the support; in this way, after washings, the support is made ready for its use, intended for its dipping into the investigational urine.

In the presence of one or both parameters involved in the determination, a complex will be formed between them and their related antibody, physically fixed on the solid support.

The support is subsequently washed, and dipped into a mixture of serum of human chorionic anti-gonadotropin conjugated with peroxidase, and benzoylecgonine conjugated with beta-galactosidase: the ratio between the two labelled compounds will be such as to enable a good detection sensitivity.

After allowing a lapse of time sufficient for the formation of the complexes (5–60 minutes), the support is further washed, and dipped into a solution of peroxidase-specific substrate (e.g., azino-benzothiazolino-sulfonate, phenol-4-amino-antipyrine, etc.), and subsequently into a second beta-galactosidase specific substrate (e.g., chlorophenol red -beta galactoside). The first solution stains in the presence of human chorionic gonadotropin; the color of the second solution is inversely proportional to the concentration of benzoylecgonine present in the investigational biological fluid.

EXAMPLE 5

(a) Preparation of the device suited for the determination of progesterone in biological fluids: milk, urine, serum and plasma Polyvinyl chloride supports, with a round-shaped extremity, are used as solid phase.

These supports are allowed to incubate with a solution, in pH 7.5 phosphate buffer, of 2.5 percent glutaraldehyde for a length of time ranging between 2 and 8 hours at 37° C. or at room temperature.

Subsequently, the supports are thoroughly washed with a solution of phosphate buffer or water.

The supports, treated as above stated, are allowed to incubate with an antiprogesterone antibody in pH 9.6 carbonate/bicarbonate buffer, at a dilution ranging between 1:100 and 1:1000 for 2 hours at 37° C., and overnight at 4° C.

At the end of the incubation, the supports are thoroughly washed with pH 7.4 saline phosphate buffer containing Tween 20 0.05 percent, and allowed to incubate in the same pH 7.4 saline buffer containing 3 percent of bovine serum albumin, and allowed to stand for 1 hour at 37° C.

This treatment has the purpose to saturate possible free sites in the polyvinyl chloride support, likely to absorb, in the subsequent steps, the progesterone aliquot to be determined, contained in the biological fluids, or still the progesterone aliquot conjugated with the enzyme.

(b) Determination of progesterone in milk

The polyvinyl chloride support is grasped with a hand, and dipped in to the milk specimen containing the investigational progesterone for a length of time ranging between 5' and 15'. At the end of the incubation, the support is transferred into a test-tube containing a solution, in pH 7 phosphate buffer, of progesterone labelled with H-R-peroxidase, and a dilution ranging between 1:1,000 and 1:1,000,000. The support is allowed to incubate for about 10 minutes, subsequently washed thoroughly with a phosphate buffer solution or water, and dipped into a test solution of TMB and perborate or $H_2O_2$, as stated in the Example 1 (c). The intensity of the color developed is inversely proportional to the concentration of progesterone present in the milk specimen; said concentration can be directly assayed by a calibration scale. It is well evident that said method is entirely extensible to the determination of progesterone in other biological fluids, such as urine, serum and plasma.

I claim:

1. A device for the qualitative diagnostic determination of a virus selected from the group consisting of herpes virus, Eppstein-Barr virus, Varicella Zoster virus, and Human T-Lymphocyte virus, consisting of a handle and conical puncture means having a pointed extremity and attached to the handle for puncture of animal or human bodies, at least a portion of the puncture means proximate the point of the conical puncture means coated with a corresponding specific antibody to the virus to be detected.

2. A method for the quantitative diagnostic determination of a virus selected from the group consisting of herpes virus, Eppstein-Barr virus, Varicella Zoster virus, and Human T-Lymphocyte virus, said method comprising puncturing an animal or human body with a pointed member having a corresponding specific antibody to the virus to be detected coated thereon proximate the point to cause the coated pointed member to be contacted by a body fluid sample for a time sufficient for a binding reaction to occur, removing unfixed substances from the coating remote from said body, thereafter contacting the coating with an enzyme-labeled antibody which is a binding partner of the virus to be determined, removing unbound labeled antibodies from the coating, thereafter contacting the coating with a detecting solution containing a substrate capable of a detecting reaction with said enzyme, and detecting the presence or absence of the product of the detecting reaction as an indication of the presence or absence of said virus in the sample.

* * * * *